(12) United States Patent
Yaguchi et al.

(10) Patent No.: US 11,848,127 B2
(45) Date of Patent: Dec. 19, 2023

(54) COMPOSITE CABLE

(71) Applicant: Hitachi Metals, Ltd., Tokyo (JP)

(72) Inventors: Atsuro Yaguchi, Tokyo (JP); Kimika Kudo, Tokyo (JP); Takanobu Watanabe, Tokyo (JP); Detian Huang, Tokyo (JP)

(73) Assignee: PROTERIAL, LTD., Tokyo (JP)

( * ) Notice: Subject to any disclaimer, the term of this patent is extended or adjusted under 35 U.S.C. 154(b) by 0 days.

(21) Appl. No.: 17/953,994

(22) Filed: Sep. 27, 2022

(65) Prior Publication Data
US 2023/0108586 A1    Apr. 6, 2023

(30) Foreign Application Priority Data
Sep. 30, 2021 (JP) .................. 2021-161080

(51) Int. Cl.
*H01B 7/22* (2006.01)
*H01B 7/04* (2006.01)
*A61B 1/00* (2006.01)

(52) U.S. Cl.
CPC .......... *H01B 7/226* (2013.01); *A61B 1/00114* (2013.01)

(58) Field of Classification Search
CPC ........ H01B 7/048; H01B 7/226; H01B 11/20; A61B 1/00018; A61B 1/00114
See application file for complete search history.

(56) References Cited

U.S. PATENT DOCUMENTS

| | | | | |
|---|---|---|---|---|
| 9,472,319 B1* | 10/2016 | Adachi | ............... | H02G 3/0437 |
| 2007/0184689 A1* | 8/2007 | Tanaka | .................. | H01B 7/423 |
| | | | | 439/86 |
| 2012/0292079 A1 | 11/2012 | Muramatsu et al. | | |
| 2013/0333917 A1* | 12/2013 | Tanabe | ................... | H01B 7/048 |
| | | | | 174/113 R |
| 2014/0209348 A1* | 7/2014 | Hayashishita | ......... | H01B 11/20 |
| | | | | 174/106 R |
| 2014/0238722 A1* | 8/2014 | Hayashishita | ......... | H01B 11/20 |
| | | | | 174/115 |
| 2014/0251651 A1* | 9/2014 | Huang | ................... | H01B 9/024 |
| | | | | 174/34 |
| 2016/0093416 A1* | 3/2016 | Huang | ............... | A61B 1/00078 |
| | | | | 174/70 R |
| 2016/0254075 A1* | 9/2016 | Huang | ................. | H01B 7/2825 |
| | | | | 174/110 AR |
| 2018/0151272 A1* | 5/2018 | Watanabe | .......... | A61B 1/00114 |

FOREIGN PATENT DOCUMENTS

JP    2013-176567 A    9/2013

* cited by examiner

*Primary Examiner* — Hoa C Nguyen
*Assistant Examiner* — Amol H Patel
(74) *Attorney, Agent, or Firm* — MCGINN I.P. LAW GROUP, PLLC.

(57) ABSTRACT

A composite cable is provided with plural wires each having a metal conductor and an insulator, a binder layer that bundles the plural wires together, a shield layer composed of a metal conductor and arranged around the binder layer, and a sheath covering around the shield layer. An outer diameter of the sheath is 2.0 mm or less. An amount of the metal conductor per unit length used in the shield layer is 0.4 times or more and 0.7 times or less than an amount of the metal conductor per unit length used in the plural wires.

9 Claims, 4 Drawing Sheets

COMPOSITE CABLE

CROSS-REFERENCE TO RELATED APPLICATION

The present patent application claims the priority of Japanese patent application No. 2021-161080 filed on Sep. 30, 2021, and the entire contents thereof are hereby incorporated by reference.

TECHNICAL FIELD

The present invention relates to a composite cable with plural electric wires each having a metal conductor and an insulator.

BACKGROUND ART

Conventionally, as a small-diameter medical cable such as an endoscopic signal cable, one including plural wires (i.e., electric wires), a binder layer for bundling the plural wires, a shield layer provided around the binder layer, and a sheath covering an outer periphery of the shield layer, is known (see e.g., Patent Literature 1).

In an endoscopic signal cable described in Patent Literature 1, plural coaxial wires (i.e., coaxial electric wires) for a drive signal system and an output signal system and plural wires (i.e., plural simple electric wires) for a power supply system are collectively bundled by an insulating binder tape spirally wound around these wires. A general shield (i.e., a collective shield, a common shield) formed by twisting a plurality of silver-plated copper alloy conductor strands (i.e., elementary wires) is provided around the binder tape, and the general shield is covered with a sheath.

CITATION LIST

Patent Literature

Patent Literature 1: JP2013-176567A

SUMMARY OF THE INVENTION

As described above, for a composite cable used for medical purposes, for example, it may be required to reduce a cable diameter to 2 mm or less. It has been confirmed by the inventors of the present application that when such a small-diameter composite cable is subjected to a bending endurance test, the test results often fail due to disconnection of one or more shield strands (i.e., the strands constituting the shield) or cracking of the sheath. Accordingly, the object of the present invention is to provide a small-diameter composite cable having high bending resistance.

To solve the aforementioned problems, one aspect of the present invention provides a composite cable, comprising:
  plural wires each having a metal conductor and an insulator;
  a binder layer that bundles the plural wires together;
  a shield layer composed of a metal conductor and arranged around the binder layer; and
  a sheath covering around the shield layer,
  wherein an outer diameter of the sheath is 2.0 mm or less,
  wherein an amount of the metal conductor per unit length used in the shield layer is 0.4 times or more and 0.7 times or less than an amount of the metal conductor per unit length used in the plural wires.

Effects of the Invention

According to the present invention, it is possible to provide a small-diameter composite cable having high bending resistance.

BEST MODE FOR CARRYING OUT THE INVENTION

Figure 1:
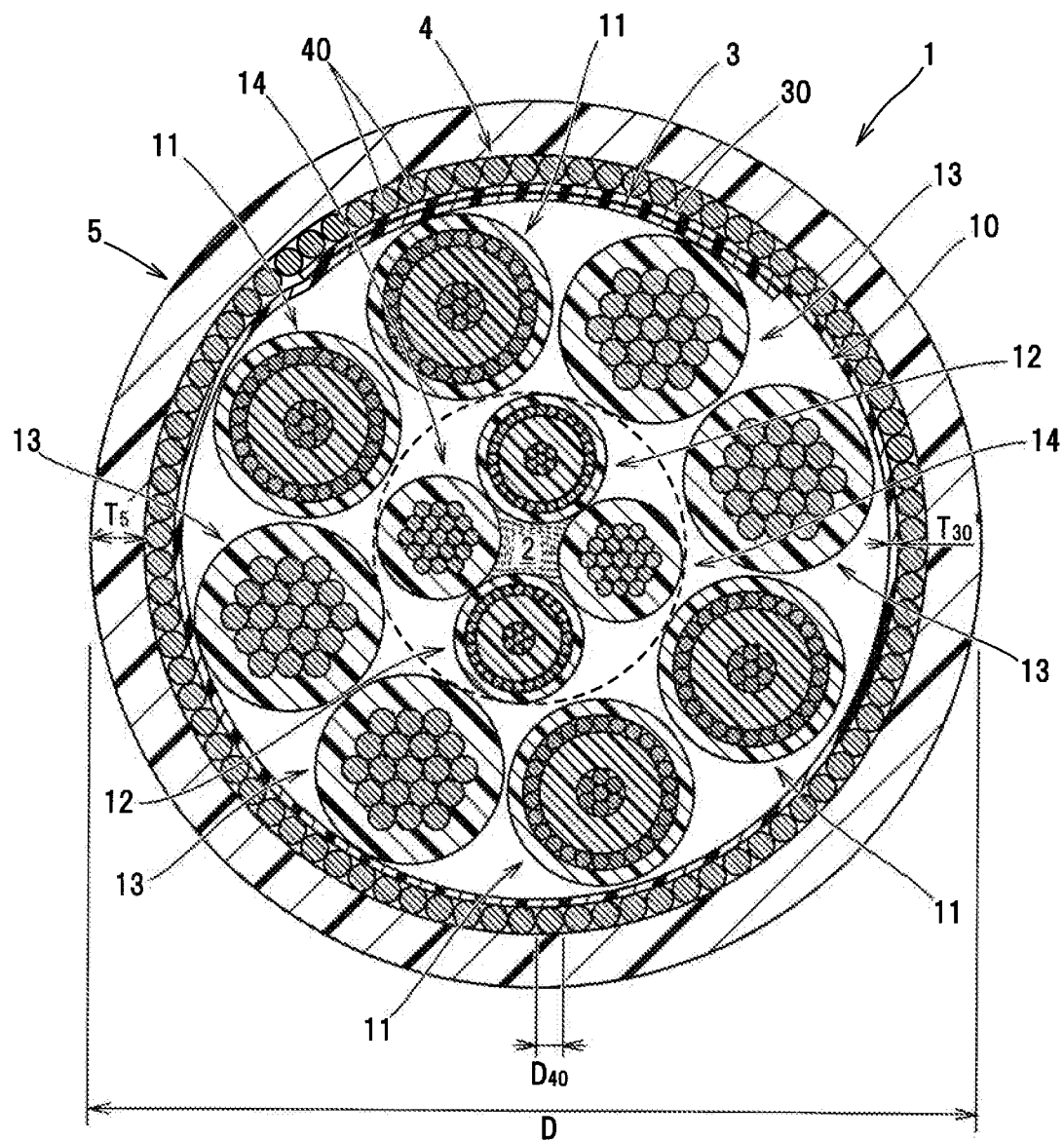
FIG. 1 is a cross-sectional view of a composite cable according to an embodiment of the present invention.

FIG. 1 is a cross-sectional view of a composite cable 1 according to the embodiment of the present invention. This composite cable 1 includes a wire group 10 composed of plural wires (i.e., electric wires) each having a metal conductor and an insulator, a filler 2 arranged in the center of the wire group 10, a binder layer 3 arranged around the wire group 10, a shield layer 4 arranged around the binder layer 3, and a sheath 5 covering around the shield layer 4. An outer diameter D (cable outer diameter) of the sheath 5 is 2.0 mm or less, and is 1.6 mm in the present embodiment.

In the present embodiment, the wire group 10 is composed of twelve electric wires consisting of four large-diameter coaxial wires 11, two small-diameter coaxial wires 12, four large-diameter simple wires 13, and two small-diameter simple wires 14. The filler 2 is, for example, a bundle of aramid fibers. The binder layer 3 bundles ten electric wires of the wire group 10. In the present embodiment, the binder layer 3 is formed by spirally winding a band-shaped binder tape 30 made of a resin such as PI (polyimide) around the wire group 10. A thickness $T_{30}$ of the binder tape 30 is, e.g., 0.01 mm. The sheath 5 is formed by extruding a thermoplastic resin such as PFA (tetrafluoroethylene-perfluoroalkyl vinyl ether copolymer). A thickness $T_5$ (average thickness) of the sheath 5 is preferably 0.07 mm or more and 0.12 mm or less. In the present embodiment, as an example, the thickness $T_5$ of the sheath 5 is 0.10 mm.

The composite cable 1 is an endoscope cable used in an endoscope having a CCD drive circuit, an A/D converter, an image memory, an image processing circuit, etc. at its distal end. The large-diameter and small-diameter coaxial wires 11 and 12 are used as signal lines for transmitting image signals and control signals. The large-diameter and small-diameter simple wires 13 and 14 are used as power lines for the power supply. The two small-diameter coaxial wires 12 and two small-diameter simple wires 14 are twisted together around the filler 2. The four large-diameter coaxial wires 11 and the four large-diameter simple wires 13 are arranged on the outer peripheries of the two small-diameter coaxial wires 12 and the two small-diameter simple wires 14, and spirally twisted.

The shield layer 4 is a laterally wound shield layer, in which plural shield strands 40 made of a metal conductor are spirally wound, and the shield layer 4 collectively shields the respective electric wires of the wire group 10. In the present embodiment, the shield layer 4 is composed of eighty-four (84) shield strands 40 as an example. The shield strand 40 is a circular cross-sectional wire made of a copper alloy. A diameter (wire diameter) $D_{40}$ of the shield strand 40 is preferably 0.03 mm or more corresponding to 48 AWG (American wire gauge) and 0.05 mm or less corresponding to 45 AWG. This is because if the diameter $D_{40}$ of the shield strand 40 is less than 0.03 mm, the shield strand 40 is likely to break, and if the diameter $D_{40}$ of the shield strand 40 exceeds 0.05 mm, the diameter of the composite cable 1 is increased. In the present embodiment, as an example, the shield strand 40 has the diameter $D_{40}$ of 0.05 mm.

In order to suppress cracking of the sheath 5 when the composite cable 1 is bent, the thickness $T_5$ of the sheath 5 is preferably 1.4 times or more and 3.0 times or less the diameter $D_{40}$ of the shield strand 40. If the thickness $T_5$ of the sheath 5 is less than 1.4 times the diameter $D_{40}$ of the shield strand 40, the strength of the sheath 5 is low, and if the thickness $T_5$ of the sheath 5 exceeds 3.0 times the diameter $D_{40}$ of the shield strand 40, the rigidity of the sheath 5 makes the shield strand 40 more likely to break and the diameter of the composite cable 1 to increase. As described above, when the thickness $T_5$ of the sheath 5 is 0.10 mm and the diameter $D_{40}$ of the shield strand 40 is 0.05 mm, the thickness $T_5$ of the sheath 5 is twice the diameter $D_{40}$ of the shield strand 40.

Figure 2:
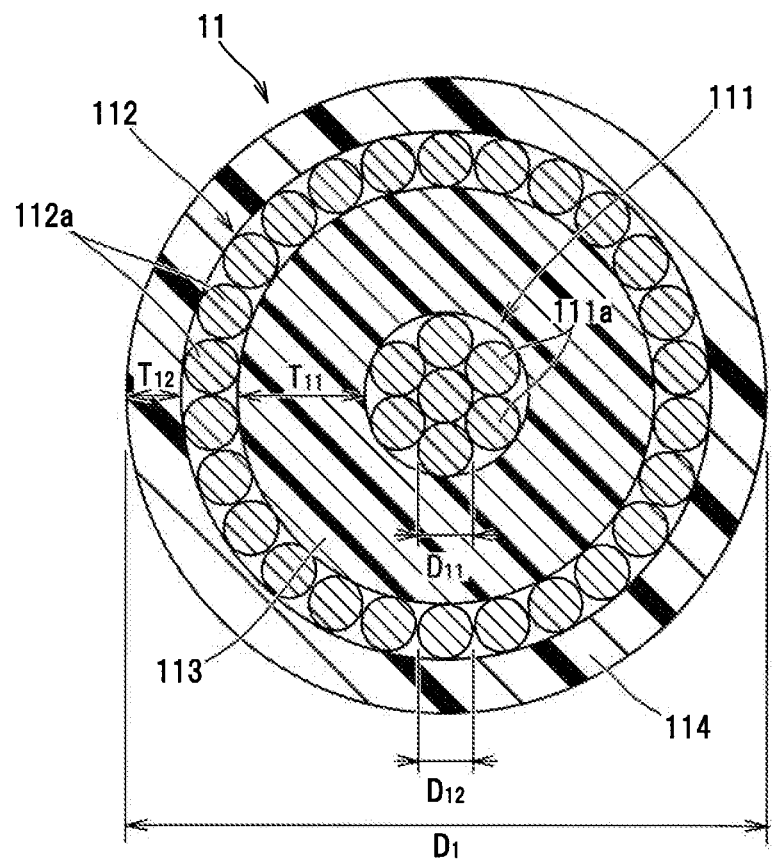
FIG. 2 is a cross-sectional view showing a large-diameter coaxial wire.

FIG. 2 is a cross-sectional view showing the large-diameter coaxial wire 11. The large-diameter coaxial wire 11 has a center conductor 111, an outer conductor 112, an insulator 113 made of a resin and arranged between the center conductor 111 and the outer conductor 112, and a jacket 114 made of a resin and arranged around the outer conductor 112. The center conductor 111 is a twisted wire obtained by twisting plural strands 111a together. The outer conductor 112 is formed by spirally winding plural strands 112 side-by-side around the insulator 113.

In the present embodiment, as an example, the center conductor 111 of the large-diameter coaxial wire 11 consists of seven (7) strands 111a, and the outer conductor 112 consists of twenty-six (26) strands 112a. These strands 111a and 112a are metal conductors made of a copper alloy and each having a circular cross-section. The center conductor 111 corresponds to 40 AWG, and a diameter $D_{11}$ of the strand 111a is 0.03 mm A diameter $D_{12}$ of the strand 112a of the outer conductor 112 is 0.03 mm. The insulator 113 and the jacket 114 are made of PFA, for example. A thickness $T_{11}$ of the insulator 113 is 0.07 mm, and a thickness $T_{12}$ of the jacket 114 is 0.03 mm. Also, an outer diameter $D_1$ of the jacket 114 is 0.35 mm.

Figure 3:
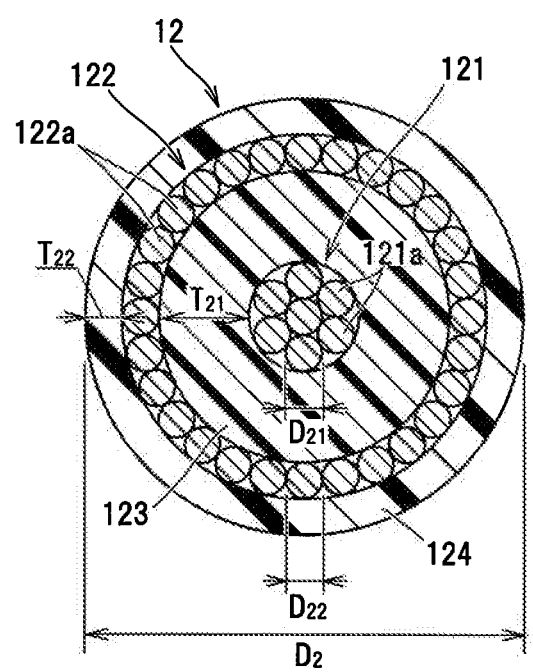
FIG. 3 is a cross-sectional view showing a small-diameter coaxial wire.

FIG. 3 is a cross-sectional view showing the small-diameter coaxial wire 12. The small-diameter coaxial wire 12 is configured similarly to the large-diameter coaxial wire 11. In other words, the small-diameter coaxial wire 12 has a center conductor 121, an outer conductor 122, an insulator 123 made of a resin and arranged between the center conductor 121 and the outer conductor 122, and a jacket 124 made of a resin and arranged around the outer conductor 122. The center conductor 121 is a twisted wire obtained by twisting plural strands 121a together, and the outer conductor 122 is formed by spirally winding the plural strands 122a side-by-side around the outer periphery of the insulator 123.

In the present embodiment, as an example, the center conductor 121 of the small-diameter coaxial wire 12 consists of seven (7) strands 121a, and the outer conductor 122 consists of twenty-eight (28) strands 122a. These strands 121a and 122a are metal conductors made of a copper alloy and each having a circular cross-section. The center conductor 121 corresponds to 44 AWG, and a diameter $D_{21}$ of the strand 121a is 0.02 mm A diameter $D_{22}$ of the strand 122a of the outer conductor 122 is 0.02 mm. The insulator 123 and the jacket 124 are made of PFA, for example. A thickness $T_{21}$ of the insulator 123 is 0.05 mm, and a thickness $T_{22}$ of the jacket 124 is 0.02 mm. An outer diameter $D_2$ of the jacket 124 is 0.25 mm.

Figure 4:
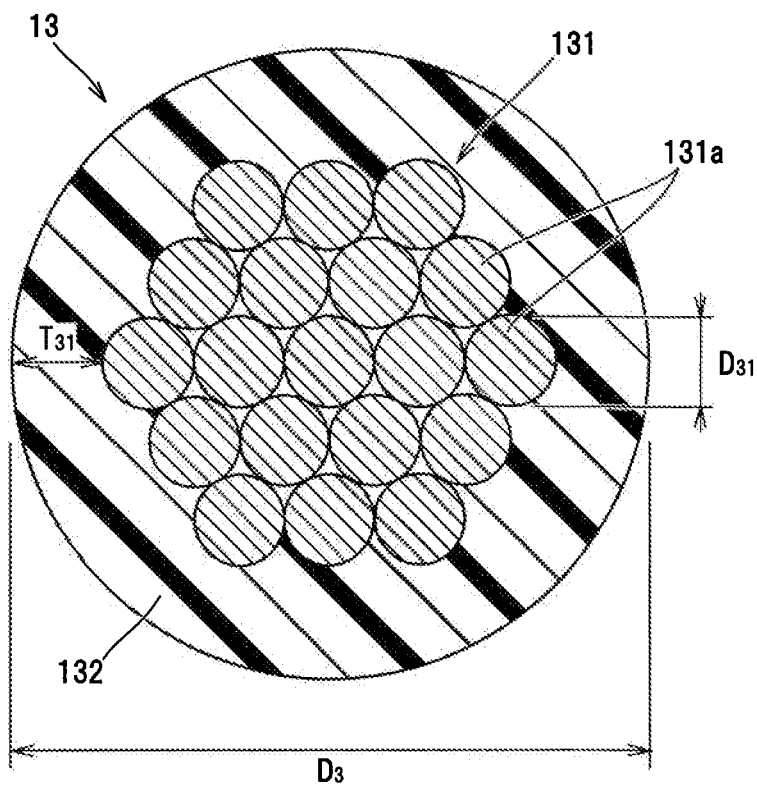
FIG. 4 is a cross-sectional view showing a large-diameter simple wire.

FIG. 4 is a cross-sectional view showing the large-diameter simple wire 13. The large-diameter simple wire 13 has a core wire 131 provided in the center and an insulator 132 made of a resin and covering the core wire 131. In the present embodiment, as an example, the core wire 131 of the large-diameter simple wire 13 is a twisted wire formed by twisting nineteen (19) strands 131a together. The strand 131a is a circular cross-sectional metal conductor made of a copper alloy. A diameter $D_{31}$ of the strand 131a is 0.05 mm. The insulator 132 is made of PFA, for example. A thickness $T_{31}$ of the insulator 132 is 0.05 mm. An outer diameter $D_3$ of the insulator 132 is 0.35 mm.

Figure 5:
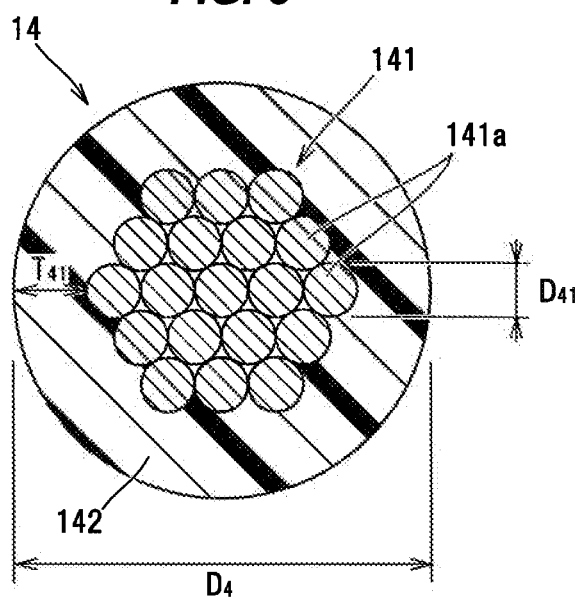
FIG. 5 is a cross-sectional view showing a small-diameter simple wire.

FIG. 5 is a cross-sectional view showing a small-diameter simple wire 14. The small-diameter simple wire 14 has a core wire 141 provided in the center and an insulator 142 made of a resin and covering the core wire 141. In the present embodiment, as an example, the core wire 141 of the large-diameter simple wire 14 is a twisted wire formed by twisting nineteen (19) strands 141a together. The strand 141a is a circular cross-sectional metal conductor made of a copper alloy. A diameter $D_{41}$ of the strand 141a is 0.03 mm. The insulator 142 is made of PFA, for example. A thickness $T_{41}$ of the insulator 142 is 0.04 mm. An outer diameter $D_4$ of the insulator 142 is 0.23 mm.

In the present embodiment, in order to increase the bending resistance of the composite cable 1, a thin shield strand 40 is used as compared to a shield strand used in a conventional small-diameter composite cable. The diameter of the shield strand used in the conventional composite cable having an outer diameter of 2 mm or less is, e.g., 0.08 mm to 0.10 mm. Also, in the present embodiment, the amount of metal conductor per unit length used in the shield layer 4 is 0.4 times or more and 0.7 times or less than the amount of metal conductor per unit length used in respective wires of the wire group 10. If this ratio is less than 0.4, disconnection is likely to occur in the shield layer 4. If this ratio exceeds 0.7, the composite cable 1 becomes thicker, making it difficult to keep the outer diameter of the cable below 2.0 mm, for example. Furthermore, in the present embodiment, a wire having a tensile strength of 320 MPa or more and a breaking elongation of 10% or more is used as the shield strand 40 in order to suppress breakage of the shield strand 40.

In the cross-section perpendicular to the longitudinal direction of the composite cable 1, when the diameter of the strand 111a of the center conductor 111 is $D_{11}$, the number of the strands 111a of the center conductor 111 is $N_{11}$, the diameter of the strand 112a of the outer conductor 112 is $D_{12}$, and the number of the strands 112a of the outer conductor 112 is $N_{12}$, the cross-sectional area $S_{11}$ of the metal conductor (in the present embodiment, copper alloy) of the large-diameter coaxial wire 11 is obtained by an equation $S_{11}=(D_{11}/2)^2 \times \pi \times N_{11}+(D_{12}/2)^2 \times \pi \times N_{12}$. Similarly, when the diameter of the strand 121a of the center conductor 121 is $D_{21}$, the number of the strands 121a of the center conductor 121 is $N_{21}$, the diameter of the strand 122a of the outer conductor 122 is $D_{22}$, and the number of the strands 122a of the outer conductor 122 is $N_{22}$, the cross-sectional area $S_{12}$ of the metal conductor of the small-diameter coaxial wire 12 is obtained by an equation $S_{12}=(D_{21}/2)^2 \times \pi \times N_{21}+(D_{22}/2)^2 \times \pi \times N_{21}$. Also, when the diameter of the strand 131a is $D_{31}$ and the number of the strands 131a is $N_{31}$, the cross-sectional area $S_{13}$ of the metal conductor of the large-diameter simple wire 13 is obtained by an equation $S_{13}=(D_{31}/2)^2 \times \pi \times N_{31}$. When the diameter of the strand 141a is $D_{41}$ and the number of the strands 141a is $N_{41}$, the cross-sectional area $S_{14}$ of the metal conductor of the small-diameter simple wire 14 is obtained by an equation $S_{14}=(D_{41}/2)^2 \times \pi \times N_{41}$.

Applying the above values of the diameter and the number of respective strands to these equations to find $S_{11}$ to $S_{14}$ gives $S_{11}=0.0233$ mm$^2$, $S_{12}=0.0110$ mm$^2$, $S_{13}=0.0373$ mm$^2$, and $S_{14}=0.0134$ mm$^2$. In the present embodiment, since the composite cable 1 includes the four large-diameter coaxial wires 11, the two small-diameter coaxial wires 12, and the four large-diameter simple wires 13, and the two small-diameter simple wires 14, the cross-sectional area $S_1$ of the metal conductor of the entire wire group 10 is obtained as 0.2914 mm$^2$ by an equation $S_1=S_{11} \times 4+S_{12} \times 2+S_{13} \times 4+S_{14} \times 2$.

On the other hand, when the diameter of the shield strand 40 is $D_{40}$ and the number of the shield strands 40 is $N_{40}$, the cross-sectional area $S_2$ of the metal conductor of the plural shield strands 40 is obtained by an equation $S_2=(D_{40}/2)^2 \times \pi \times N_{40}$. Applying the above values of the diameter and the number of the shield strands 40 to this equation to find $S_2$ gives $S_2=0.1649$ mm$^2$. This value is approximately 0.566 times the value of $S_1$. That is, in the present embodiment, the amount of metal conductor per unit length used in the shield layer 4 is about 0.566 times the amount of metal conductor per unit length used in the respective electric wires of the wire group 10.

(Evaluation of Durability of the Composite Cable)

The composite cable 1 constructed as described above has a bending endurance (i.e., endurable number of bending cycles) of 50,000 times or more under the condition with a bending diameter of 15 mm, a bending angle of ±90° or more, and a load of 100 g. The composite cable 1 has a twisting (torsion) resistance (i.e., endurable number of twisting cycles) of 100,000 times or more under the condition with a twisting pitch of 200 mm, a bending angle of ±180° or more, and a load of 150 g. This test result is the result of conducting a bending endurance test and a twisting (torsion) endurance test using a bending tester and a twisting (torsion) tester described below.

Figure 6:
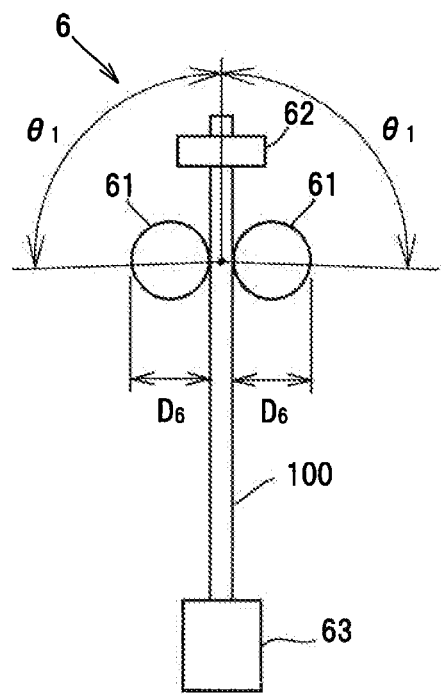
FIG. 6 is a configuration diagram showing a configuration example of a bending tester used for a bending endurance test.

FIG. 6 is a configuration diagram showing a configuration example of a bending tester 6 used for the bending endurance test. The bending tester 6 has a pair of bending diameter setting jigs 61, 61, a test piece fixing portion 62 and a weight 63. The bending diameter setting jigs 61, 61 are cylindrical, and their diameter $D_6$ is the bending diameter. One end of a test piece 100 obtained by cutting the composite cable 1 into a predetermined length is fixed to the test piece fixing portion 62. The weight 63 having a weight corresponding to the applied load is fixed to the other end of the test piece 100. In the bending endurance test, a portion of the test piece 100 in the longitudinal direction is sandwiched between the pair of bending diameter setting jigs 61, 61, and the test piece fixing portion 62 is reciprocated in an arc within the range of the angle $\pm\theta_1$ corresponding to the bending angle.

Figure 7:
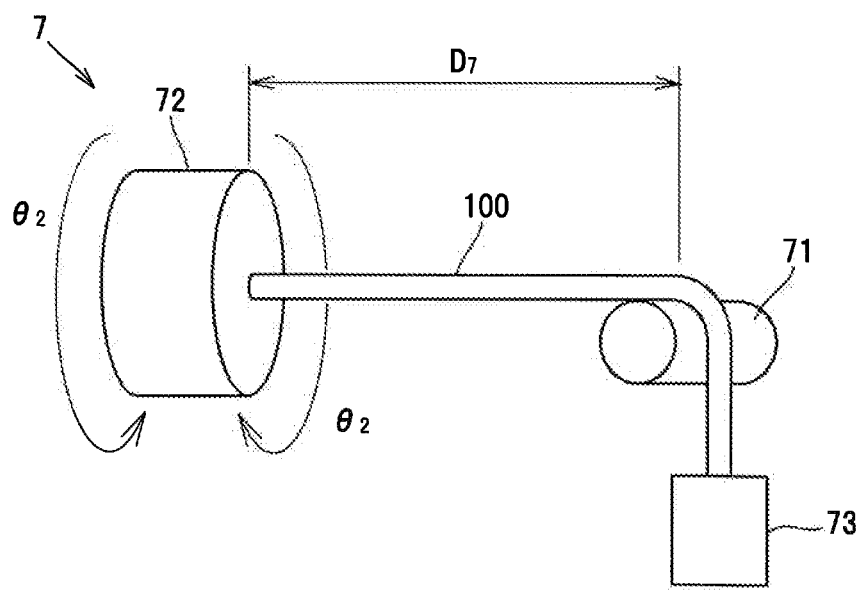
FIG. 7 is a configuration diagram showing a configuration example of a twisting tester used for a twisting endurance test.

FIG. 7 is a configuration diagram showing a configuration example of a twisting (i.e., torsion) tester 7 used for the twisting (i.e., torsion) endurance test. The twisting tester 7 has a cylindrical support jig 71, a disk-shaped twisting jig 72, and a weight 73. One end of the test piece 100 is fixed to the twisting jig 72. The weight 73 having a weight corresponding to the applied load is fixed to the other end of the test piece 100. A distance $D_7$ between the twisting jig 72 and the support jig 71 is set to a dimension corresponding to the twisting pitch. The twisting jig 72 reciprocates and rotates within a range of angles $\pm\theta_2$ corresponding to the bending angle.

In the bending endurance test and the twisting endurance test of the composite cable 1, it was confirmed whether there was any appearance abnormality such as cracking of the sheath 5 and whether there was any disconnection of the shield strand 40 or each wire of the wire group 10 every 10,000 times. The test was continued when no abnormalities were observed. In the bending endurance test, these abnormalities were not observed even after 50,000 times, and in the twisting endurance test, these abnormalities were not observed even after 100,000 times.

Effect of Embodiment

According to the embodiment described above, since the amount of metal conductor per unit length used in the shield layer 4 is 0.4 times or more and 0.7 times or less than the amount of metal conductor per unit length used in respective wires of the wire group 10, the composite cable 1 can be thinned to 2.0 mm or less while having high bending resistance. Further, according to the present embodiment, since the thickness $T_5$ of the sheath 5 is 1.4 times or more and 3.0 times or less the diameter $D_{40}$ of the shield strand 40 and the diameter $D_{40}$ of the shield strand 40 is 0.03 mm or more and 0.05 mm or less, it is possible to reduce the diameter of the composite cable 1 while ensuring the strength of the sheath 5, and to suppress breakage of the shield strand 40 as well.

Modified Example

In the above embodiment, the case where the shield strand 40 has a tensile strength of 320 MPa or more and a breaking elongation of 10% or more has been explained. As the shield strand 40, a shield strand having a tensile strength of 380 MPa or more and a breaking elongation of 5% or more can be used. A composite cable 1 using such a shield strand 40 having a tensile strength of 380 MPa or more and a breaking elongation of 5% or more can also obtain high bending resistance.

Summary of Embodiments

Next, the technical ideas grasped from the above-described embodiment will be described with reference to the symbols and the like in the embodiment. However, each reference numeral in the following description does not limit the constituent elements in the scope of claims to the members and the like that are specifically indicated in the embodiment.

According to the feature [1], a composite cable 1 includes plural wires 11 to 14 each having a metal conductor and an insulator, a binder layer 3 that bundles the plural wires 11 to 14 together, a shield layer 4 composed of a metal conductor and arranged around the binder layer 3, and a sheath 5 covering around the shield layer 4, wherein an outer diameter D of the sheath 5 is 2.0 mm or less, wherein an amount of the metal conductor per unit length used in the shield layer 4 is 0.4 times or more and 0.7 times or less than an amount of the metal conductor per unit length used in the plural wires 11 to 14.

According to the feature [2], in the composite cable 1 as described in the feature [1], the shield layer 4 is a laterally wound shield layer including plural shield strands 40 composed of a metal conductor and being spirally wound.

According to the feature [3], in the composite cable 1 as described in the feature [2], an average thickness $T_5$ of the sheath 5 is 1.4 times or more and 3.0 times or less than a diameter $D_{40}$ of each of the plural shield strands 40.

According to the feature [4], in the composite cable 1 as described in the feature [2] or [3], each of the plural shield strand 40 has a diameter $D_{40}$ of 0.03 mm or more and 0.05 mm or less.

According to the feature [5], in the composite cable 1 as described in any one of the features [2] to [4], each of the plural shield strands 40 has a tensile strength of 320 MPa or more and a breaking elongation of 10% or more.

According to the feature [6], in the composite cable 1 as described in any one of the features [2] to [4], each of the plural shield strands 40 has a tensile strength of 380 MPa or more and a breaking elongation of 5% or more.

According to the feature [7], in the composite cable 1 as described in any one of the features [1] to [6], a first group wire 13, 14 of the plural wires 11 to 14 is a simple wire including a core wire 131, 141 composed of a metal conductor, and an insulator 132, 142 covering the core wire 131, 141, and a second group wire 11, 12 of the plural wires 11 to 14 is a coaxial wire including a center conductor 111, 121, an outer conductor 112, 122, and an insulator 113, 114 arranged between the center conductor 111, 121 and the outer conductor 112, 122.

According to the feature [8], in the composite cable 1 as described in any one of the features [1] to [7], a bending endurance is 50,000 times or more under the condition with a bending diameter of 15 mm, a bending angle of ±90° or more, and a load of 100 g.

According to the feature [9], in the composite cable 1 as described in any one of the features [1] to [8], a twisting resistance is 100,000 times or more under the condition with a twisting pitch of 200 mm, a bending angle of ±180° or more, and a load of 150 g.

The embodiment of the present invention has been described above, but the embodiment described above does not limit the invention according to the scope of claims. Also, it should be noted that not all combinations of features described in the embodiments are essential to the means for solving the problems of the invention.

Moreover, the present invention can be modified appropriately without departing from the gist thereof. For example, in the above embodiment, the composite cable 1 includes four large-diameter coaxial wires 11, two small-diameter coaxial wires 12, four large-diameter simple wires 13, and two small-diameter simple wires 14. However, the number and types of electric wires are not limited to this configuration, and it is possible to configure a composite cable by combining plural wires according to the application. Moreover, the application of the composite cable is not limited to medical cables such as endoscopic cables, and the composite cable of the present invention can be used for various applications that require a small diameter and high bending resistance.

The invention claimed is:

1. A composite cable, comprising:
   plural wires each having a metal conductor and an insulator;
   a binder layer that bundles the plural wires together;
   a shield layer composed of a metal conductor and arranged around the binder layer; and
   a sheath covering around the shield layer,
   wherein an outer diameter of the sheath is 2.0 mm or less,
   wherein an amount of the metal conductor per unit length used in the shield layer is 0.4 times or more and 0.7 times or less than an amount of the metal conductor per unit length used in the plural wires.

2. The composite cable, according to claim 1, wherein the shield layer is a laterally wound shield layer including plural shield strands composed of a metal conductor and being spirally wound.

3. The composite cable, according to claim 2, wherein an average thickness of the sheath is 1.4 times or more and 3.0 times or less than a diameter of each of the plural shield strands.

4. The composite cable, according to claim 2, wherein each of the plural shield strand has a diameter of 0.03 mm or more and 0.05 mm or less.

5. The composite cable, according to claim 2, wherein each of the plural shield strands has a tensile strength of 320 MPa or more and a breaking elongation of 10% or more.

6. The composite cable, according to claim 2, wherein each of the plural shield strands has a tensile strength of 380 MPa or more and a breaking elongation of 5% or more.

7. The composite cable, according to claim 1, wherein a first group wire of the plural wires is a simple wire including a core wire composed of a metal conductor, and an insulator covering the core wire, and a second group wire of the plural wires is a coaxial wire including a center conductor, an outer conductor, and an insulator arranged between the center conductor and the outer conductor.

8. The composite cable, according to claim 1, wherein a bending endurance is 50,000 times or more under a condition with a bending diameter of 15 mm, a bending angle of ±90° or more, and a load of 100 g.

9. The composite cable, according to claim 1, wherein a twisting resistance is 100,000 times or more under a condition with a twisting pitch of 200 mm, a bending angle of ±180° or more, and a load of 150 g.

* * * * *